United States Patent
Jensen et al.

(10) Patent No.: US 9,775,861 B1
(45) Date of Patent: Oct. 3, 2017

(54) DRY EYE COMPOSITION AND METHOD FOR PREPARING THE COMPOSITION

(71) Applicants: Paul S. Jensen, Bellevue, WA (US); Isaiah U. Lieberman, Issaquah, WA (US)

(72) Inventors: Paul S. Jensen, Bellevue, WA (US); Isaiah U. Lieberman, Issaquah, WA (US)

(*) Notice: Subject to any disclaimer, the term of this patent is extended or adjusted under 35 U.S.C. 154(b) by 0 days.

(21) Appl. No.: 14/864,812

(22) Filed: Sep. 24, 2015

Related U.S. Application Data

(60) Provisional application No. 62/056,373, filed on Sep. 26, 2014.

(51) Int. Cl.
| | | |
|---|---|---|
| *A61K 31/765* | (2006.01) | |
| *A61K 9/06* | (2006.01) | |
| *A61K 47/38* | (2006.01) | |
| *A61K 47/02* | (2006.01) | |
| *A61K 9/00* | (2006.01) | |

(52) U.S. Cl.
CPC .......... *A61K 31/765* (2013.01); *A61K 9/0048* (2013.01); *A61K 9/06* (2013.01); *A61K 47/02* (2013.01); *A61K 47/38* (2013.01)

(58) Field of Classification Search
CPC .......... A61K 31/765; A61K 8/02; A61K 8/86
See application file for complete search history.

(56) References Cited

U.S. PATENT DOCUMENTS

| 8,506,539 B2 * | 8/2013 | Guillon ................. A61F 7/034 604/291 |
|---|---|---|
| 2007/0254841 A1 * | 11/2007 | Ousler, III ........... A61K 9/0048 514/569 |
| 2007/0269537 A1 * | 11/2007 | Gupta ................. A61K 8/0212 424/740 |

* cited by examiner

*Primary Examiner* — Zohreh Fay
(74) *Attorney, Agent, or Firm* — Patrick J. S. Inouye; Krista A. Wittman

(57) ABSTRACT

An ophthalmic composition of water soluble ingredients provides additional moisture to the eye by promoting moisture absorption from the air and providing long lasting relief. The composition can include two groups of ingredients, one a liquid and the other a solid. Together, the ingredients form a substance that ranges from a liquid to a gel. Benefits of such composition include longer lasting symptom relief with less applications and increased moisture production.

8 Claims, No Drawings

DRY EYE COMPOSITION AND METHOD FOR PREPARING THE COMPOSITION

CROSS-REFERENCE TO RELATED APPLICATION

This non-provisional patent application claims priority under 35 U.S.C. §119(e) to U.S. Provisional Patent Application, Ser. No. 62/056,373, filed Sep. 26, 2014, the disclosure of which is incorporated by reference.

FIELD

The invention relates in general to ophthalmic compositions, and in particular, to dry eye and dry skin compositions and methods for preparing the compositions.

BACKGROUND

Dry eye is one of the most common ophthalmologic problems experienced by individuals. Dry eye occurs when an individual fails to produce a sufficient quantity or quality of tears to lubricate and nourish the eye, such as due to aging, long-term contact lens wear, environmental effects, or as a side effect of certain medications, including antihistamines and antidepressants. Further, a failure to produce tears or to produce an adequate quantity or quality of tears can occur based on an inability of the eyelids to close completely over the eye, eyelid disease, and a deficiency of tear-producing glands. Individuals with dry eye often experience symptoms of dryness, scratchiness, red eyes, and a burning sensation that is irritating and uncomfortable.

Depending on the cause, dry eye can be considered a chronic and often progressive condition that can be managed via eye drops, topical preparations, change in environment, change in nutrition, or medication, as well as other means. In mild cases, dry eye is generally managed using eye drops that can be obtained over the counter or via a prescription from a doctor to supplement tear production. However, some eye drops are more effective than others for treating dry eye and most provide only a short period of relief, thus, requiring many applications throughout the day. Topical preparations are also commonly used to provide dry eye relief. However, conventional topical preparations generally only include small amounts of moisturizers, and thus, only provide short periods of relief. Like eye drops, gels also only provide a short period of relief, while ointments, which are applied to the eye, provide a longer relief period. Yet, ointments can cause blurred vision and can be difficult to apply.

Accordingly, there remains a need for a dry eye composition that provides long lasting ocular comfort that is easy to apply and provides alleviations of dry eye symptoms. Preferably, the composition does not blur vision.

SUMMARY

Currently, eye drops and ointments are frequently recommended for treating dry eye. However, conventional products include water-soluble ingredients in small amounts and offer only short periods of relief with multiple applications to provide longer periods of comfort. A composition of water soluble ingredients in a much higher concentration provides additional moisture to the eye by promoting moisture absorption from the air and provides long lasting relief. The composition can include two groups of ingredients, one a liquid and the other a solid. Together, the ingredients form a substance that ranges from a cream to an ointment to a semi-solid. Benefits of such composition include longer lasting symptom relief with less applications and increased moisture production.

Still other embodiments will become readily apparent to those skilled in the art from the following detailed description, wherein are described embodiments by way of illustrating the best mode contemplated. As will be realized, other and different embodiments are possible and their several details are capable of modifications in various obvious respects, all without departing from the spirit and the scope. Accordingly, the drawings and detailed description are to be regarded as illustrative in nature and not as restrictive.

DETAILED DESCRIPTION

Individuals with dry eye can experience a multitude of symptoms, including eye dryness, scratchiness, red eyes, a burning sensation, blurred vision, sensitivity to light and eye fatigue. Relief of dry eye symptoms can occur, inter alia, via eye drops or other lubricants, medication, and a change of environmental setting. Eye drops and gels are often recommended due to their ease of application, but only provide a short period of relief. In contrast, ointments provide longer lasting relief, but are difficult to apply. Further, currently available gels and ointments include water-soluble ingredients in small amounts that do not provide lasting relief.

A composition of water soluble ingredients promotes absorption of moisture from the air to increase moisture on the surface of the eye. The water soluble ingredients include a liquid and a solid that, when combined, form a substance that varies between a cream, ointment, or semi-solid. The first group includes a solid polyethylene glycol (PEG), while the second group includes a liquid, such as a modified glycerin, commonly known as Glycereth. Solid PEGs can have a molecular weight from 1400 to 9000.

The glycerin is modified by adding PEG adducts on one or more of the hydroxyl groups of the glycerin. Each modified form of glycerin is then identified by a number from one to 30, which represents a total number of ethoxy groups attached to the three hydroxyl groups of the glycerin. The total number of ethoxy groups is provided as an average. For example, for Glycereth 26, each modified glycerin has an average of 26 ethoxy groups. As more ethoxy groups are added, the vapor pressure is reduced.

One exemplary ophthalmic composition is a creamy gel for dry eye relief that is prepared with the components and amount listed in the table below:

TABLE 1

| Component | Minimum Amount | Maximum Amount | Preferred Amount |
|---|---|---|---|
| PEG 3350 | 10.0% | 80.0% | 60.0% |
| Glycereth 26 | 10.0% | 80.0% | 15.0% |
| $H_2O$ | 10.0% | 80.0% | 24.1% |
| NaCl | 0.0% | 0.9% | 0.9% |

The values provided in the table above specify an amount by weight based on a total weight of the composition. Although PEG 3350 is a listed component, all grades of PEG from PEG 1400 to PEG 9000 are possible in lieu of PEG 3350. However, PEG 3350 has a medium molecular weight, and is readily available and easiest to procure. When a form of PEG is used with a higher molecular weight, a lesser amount of the PEG is needed, while a larger amount of water is required to obtain a desired consistency. Glycereth 26 has a higher molecular weight than many other forms of Glycereth and a slower evaporation weight, which results in longer lasting relief of dry eye symptoms. Glycereth 26 can be obtained, for example, from Lipo Chemicals Inc., Paterson, N.J., as Liponic EG-1. However, in a further embodiment, different forms of Glycereth can be used, including Glycereth 1 through 30, in the amounts provided in the table above. Water is added to the combination of PEG and Glycereth to generate a composition that is of a proper viscosity to be applied to a patient's eye. The proper viscosity can be anything softer than a solid, such that the composition can be applied to a patient's eye. The sodium chloride can be added to the PEG-Glycereth combination to imitate real tears, which generally include 0.9% sodium chloride. The sodium chloride can equalize the ophthalmic composition and prevent stinging upon application of the composition. However, in a further embodiment, the sodium chloride can be removed from the composition described above in Table 1. In yet a further embodiment, the Glycereth can be replaced with any liquid polyethylene glycol, in the same amounts listed in the table above for Glycereth.

To prepare the composition, amounts of the components listed in the above-identified table are determined. Next, all the components are combined at the same time in the determined amounts and heated to about 130 to 150 degrees until the PEG is completely dissolved using conventional methods well known in the art. Once dissolved, the combined solution is stirred while cooling until a white creamy semi-solid, such as a gel, is formed.

The semi-solid ophthalmic composition described above is self-preserving and can be stored in a plastic tube, bottle, or eye drop dispenser for providing to a patient in need of dry eye relief. The appearance and form of the ophthalmic composition is a white semi-solid or gel, and the composition is intended to be available to patients without a prescription. In a preferred embodiment, the patient applies the ophthalmic composition to the eye, specifically, the inferior palperbral conjunctiva, via an eye dropper or a single use applicator. If the patient wears contact lenses, the contact lenses should be removed prior to application of the ophthalmic composition. A single use application can include the appropriate amount of the ophthalmic composition, while the eye dropper can be metered to release one to two drops.

In a further embodiment, the patient can squeeze the ophthalmic composition out of the tube or bottle onto his finger or another object, such as a cotton ball or Q-tip. Subsequently, the patient applies the ophthalmic composition to his eye, particularly, the inferior palperbral conjunctiva via the finger or other object. The ophthalmic composition should be applied to each eye affected by dry eye symptoms, on an as needed basis. The ophthalmic composition can provide longer relief from dry eye than currently available eye solutions. Effectiveness of the ophthalmic composition can last up to a maximum of 18 hours and one or two applications of the ophthalmic composition per day may be appropriate. However, additional applications may be necessary.

Another exemplary composition for dry eye relief is prepared with the components and amounts listed in the table below:

TABLE 2

| Component | Minimum Amount | Maximum Amount | Preferred Amount |
| --- | --- | --- | --- |
| PEG 3350 | 10.0% | 59.1% | 19.6% |
| Glycereth 26 | 10.0% | 59.1% | 30.0% |
| $H_2O$ | 30.0% | 79.1% | 50.0% |
| Carboxymethylcellulose Sodium | 0.1% | 3.0% | 00.4% |

The values provided in the table above specify an amount by weight based on a total weight of the composition. Although PEG 3350 is a listed component, all grades of PEG from PEG 1400 to PEG 9000 are possible in lieu of PEG 3350. However, PEG 3350 has a medium molecular weight, and is readily available and easiest to procure. When a form of PEG is used with a higher molecular weight, a lesser amount of the PEG is needed, while a larger amount of water is required to obtain a desired consistency. Glycereth 26 has a higher molecular weight than many other forms of Glycereth and a slower evaporation rate, which results in longer lasting relief of dry eye symptoms. Glycereth 26 can be obtained, for example, from Lipo Chemicals Inc., Paterson, N.J., as Liponic EG-1. However, in a further embodiment, different forms of Glycereth can be used, including Glycereth 1 through 30, in the amounts provided in the table above. Water is added to the combination of PEG and Glycereth to help dissolve the solid PEG and generate a composition that is the proper viscosity to be applied to a patient's eye. The proper viscosity can be anything softer than a solid, such that the composition can be applied to a patient's eye. The carboxymethylcellulose sodium acts as a thickener and can be obtained from The Dow Chemical Company, under the name Walocel CRT. In a further embodiment, the Glycereth can be replaced with any liquid polyethylene glycol, in the same amounts listed in the table above for Glycereth.

To prepare the composition, amounts of the components listed in the above-identified table are determined. Next, all the components are all combined in the determined amounts and heated to about 180 degrees until the PEG and Carboxymethylcellulose Sodium are completely dissolved using conventional methods well known in the art. Once dissolved, the combined solution is allowed to cool, forming semi-solid, such as a colorless transparent gel.

The semi-solid ophthalmic composition described above is self-preserving and can be stored in a plastic tube, bottle, or eye drop dispenser for providing to a patient in need of dry eye relief. The appearance and form of the ophthalmic composition is a transparent gel that can be slightly runny, and the composition is intended to be available to patients without a prescription. In a preferred embodiment, the patient applies the ophthalmic composition to the eye, specifically, the inferior palperbral conjunctiva, via an eye dropper or a single use applicator. If the patient wears contact lenses, the contact lenses should be removed prior to application of the ophthalmic composition. A single use application can include the appropriate amount of the ophthalmic composition, while the eye dropper can be metered to release one to two drops.

In a further embodiment, the patient can squeeze the ophthalmic composition out of the tube or bottle onto his finger or another object, such as a cotton ball or Q-tip. Subsequently, the patient applies the ophthalmic composition to his eye, particularly, the inferior palperbral conjunctiva via the finger or other object. The ophthalmic composition should be applied to each eye affected by dry eye symptoms, on an as needed basis. The ophthalmic composition can provide longer relief from dry eye than currently available eye solutions. Effectiveness of the ophthalmic composition can last up to a maximum of 18 hours and one or two applications of the ophthalmic composition per day may be appropriate. However, additional applications may be necessary.

Another exemplary composition for dry eye relief is prepared with the components and amounts listed in the table below:

TABLE 3

| Component | Minimum Amount | Maximum Amount | Preferred Amount |
|---|---|---|---|
| PEG 3350 | 10.0% | 59.9% | 19.6% |
| Glycereth 26 | 10.0% | 59.9% | 30.0% |
| NaCl | 0.0% | 0.9% | 0.9% |
| Carboxymethylcellulose Sodium | 0.1% | 3.0% | 00.4% |
| H20 | 30.0 | 70.0 | 49.1 |

The values provided in the table above specify an amount by weight based on a total weight of the composition. Although PEG 3350 is a listed component, all grades of PEG from PEG 1400 to PEG 9000 are possible in lieu of PEG 3350. However, PEG 3350 has a medium molecular weight, and is readily available and easiest to procure. When a form of PEG is used with a higher molecular weight, a lesser amount of the PEG is needed, while a larger amount of water is required to obtain a desired consistency. Glycereth 26 has a higher molecular weight than many other forms of Glycereth and a slower evaporation rate, which results in longer lasting relief of dry eye symptoms. Glycereth 26 can be obtained, for example, from Lipo Chemicals Inc., Paterson, N.J., as Liponic EG-1. However, in a further embodiment, different forms of Glycereth can be used, including Glycereth 1 through 30, in the amounts provided in the table above. The sodium chloride can be added to the PEG-Glycereth combination to imitate real tears, which generally include 0.9% sodium chloride. The sodium chloride can equalize the ophthalmic composition and prevent stinging upon application of the composition. The carboxymethylcellulose sodium acts as a thickener and can be obtained from The Dow Chemical Company, under the name Walocel CRT. In a further embodiment, the Glycereth can be replaced with any liquid polyethylene glycol, in the same amounts listed in the table above for Glycereth.

To prepare the composition, amounts of the components listed in the above-identified table are determined. Next, all the components are combined in the determined amounts and heated to about 180 degrees until the PEG and Carboxymethylcellulose Sodium are completely dissolved using conventional methods well known in the art. Once dissolved, the combined solution is allowed to cool, forming a colorless transparent gel.

The semi-solid ophthalmic composition described above is self-preserving and can be stored in a plastic tube, bottle, or eye drop dispenser for providing to a patient in need of dry eye relief. The appearance and form of the ophthalmic composition is a transparent gel that can be slightly runny. In a preferred embodiment, the patient applies the ophthalmic composition to the eye, specifically, the inferior palperbral conjunctiva, via an eye dropper or a single use applicator. If the patient wears contact lenses, the contact lenses should be removed prior to application of the ophthalmic composition. A single use application can include the appropriate amount of the ophthalmic composition, while the eye dropper can be metered to release one to two drops.

In a further embodiment, the patient can squeeze the ophthalmic composition out of the tube or bottle onto his finger or another object, such as a cotton ball or Q-tip. Subsequently, the patient applies the ophthalmic composition to his eye, particularly, the inferior palperbral conjunctiva via the finger or other object. The ophthalmic composition should be applied to each eye affected by dry eye symptoms, on an as needed basis. The ophthalmic composition can provide relief from dry eye up to a maximum of 18 hours and one or two applications of the ophthalmic composition per day may be appropriate. However, additional applications may be necessary.

The minimum and maximum amount ranges listed in Tables 1 through 3 were determined through testing of different compositions within those ranges. Specifically, the minimum and maximum amounts are based on a state of the associated compositions. For instance, in amounts outside of the identified minimum and maximum ranges, the composition may become solid or liquid and thus, inappropriate for proper application to the eye.

Further, ophthalmic compositions as outlined in the preferred amounts in each of the Tables 1 through 3, were tested on individuals. The composition in Table 2, in the preferred amounts, was given to 38 individuals. The test conditions were based on standard clinical techniques and no harm was caused to any of the individuals' eyes. Most of the individuals reported substantial improvement in dry eye symptoms, with only two reporting no improvement. With regards to duration of the dry eye symptom relief, only one of the 38 individuals needed to apply the ophthalmic composition of Table 2 more than twice per day. Whereas, most conventional eye drops require application every one to two hours to ensure that dry eye symptoms are relieved. Meanwhile, the ophthalmic composition, described above in Table 1 was provided, in the preferred amounts, to around five individuals. The test conditions were based on standard clinical techniques and no harm was caused to any of the individuals' eyes. Over all, the individuals experienced an improvement in dry eye symptoms, including a duration of relief, but also experienced a mild burning sensation that lasted no longer than ten seconds after application of the ophthalmic composition. Additionally, the ophthalmic composition of Table 3, in the preferred amounts, was tested on around five individuals. The individuals experienced relief of dry eye symptoms, including a duration of the relief. However, the salt was difficult to get evenly distributed within the composition.

The dry eye solutions can be slightly modified to prepare a cream or gel for alleviating dry skin, including providing itch relief. One exemplary composition for relief of dry skin is prepared with the components and amount listed in the table below:

TABLE 4

| Component | Minimum Amount | Maximum Amount | Preferred Amount |
|---|---|---|---|
| PEG 3350 | 5% | 95% | 12.0% |
| Glycereth 26 | 5% | 95% | 88.0% |

The composition formed from the components in the table above include a higher percentage of active ingredients than conventional skin compositions. Additionally, since the above-identified skin composition does not include water, the composition will not dry out as conventional skin compositions tend to do. Most conventional skin moisturizers are oil-based and prevent drying by hindering the evaporation of moisture already present. This composition, by comparison, acts by absorbing moisture from the air.

Although PEG 3350 is a listed component, all grades of PEG from PEG 1400 to PEG 9000 are possible in lieu of PEG 3350. However, PEG 3350 has a medium molecular weight, and is readily available and easiest to procure. When a form of PEG is used with a higher molecular weight, a lesser amount of the PEG is needed, while a larger amount of water is required to obtain a desired consistency. Glycereth 26 has a higher molecular weight than many other forms of Glycereth and a slower evaporation rate, which results in longer lasting relief of dry skin symptoms, including itching. Glycereth 26 can be obtained, for example, from Lipo Chemicals Inc., Paterson, N.J., as Liponic EG-1. However, in a further embodiment, different forms of Glycereth can be used, including Glycereth 1 through 30, in the amounts provided in the table above. For example, Glycereth 7 can be obtained, for example, from Lipo Chemicals Inc., Paterson, N.J., as Liponic EG-7. Also, as provided in the table above, the range of a PEG to Glycereth ratio can vary from a 5% PEG and 95% Glycereth to a 95% PEG and 5% Glycereth. As the percentage of PEG increases, the thicker the skin composition becomes. In one embodiment, 50% of PEG is a maximum amount to prevent the skin composition from becoming too hard. If too hard, the skin composition is difficult to apply. In a further embodiment, the Glycereth can be replaced with any liquid polyethylene glycol, in the same amounts listed in the table above for Glycereth.

Once a ratio has been selected, the components, PEG 3350 and Glycereth 7, are combined and heated to about 130 to 150 degrees until the PEG is completely dissolved. Once dissolved, the combined solution is stirred while cooling until a cream or ointment is formed. The skin composition can be stored in a plastic tube or bottle for providing to a patient in need of relief. The patient squeezes the skin composition out of the tube or bottle onto his hands or fingers and rubs the cream into areas of dry skin. The skin composition should be applied as needed. This skin composition is intended for use on rashes or itchy areas of skin that are caused by dryness or other physical conditions, rather than for conditions that require medication, such as psoriasis or eczema.

The skin composition, described above in the preferred amounts, has been used by about 20 individual human subjects for up to two years. Three of the individuals found the skin composition to be of marginal use, while three found the skin composition comparable with existing products. The remaining individuals found the skin composition to be superior to existing products by reducing a level of itching within minutes after application. Further, the skin composition has the ability to relieve dry skin symptoms, such as itching, throughout the day via a single application, as long as the patient is not excessively sweating or going swimming. When needed, the skin composition is easily removable from the skin and clothing.

While the invention has been particularly shown and described as referenced to the embodiments thereof, those skilled in the art will understand that the foregoing and other changes in form and detail may be made therein without departing from the spirit and scope of the invention.

What is claimed is:

1. An ophthalmic composition, consisting of:
   between 10% and 25% weight of polyethylene glycol;
   between 15% and 30% weight of glycereth;
   Carboxymethylcellulose Sodium; and
   water,
   wherein the composition is a viscoelastic gel that is formulated for ophthalmic administration.

2. The composition of claim 1, wherein the polyethylene glycol is polyethylene glycol 3350.

3. The composition of claim 1, wherein the glycereth is glycereth 26.

4. The composition of claim 1, wherein the composition is useful for at least one of increasing ocular comfort and for providing relief of dry eye symptoms.

5. The composition of claim 1, wherein the composition is contained in at least one of a plastic tube, bottle, and eye drop dispenser.

6. The composition of claim 1, wherein the composition is applied at least once a day to one or more eyes.

7. The composition of claim 6, wherein the composition is applied to the inferior palperbral conjunctiva of the one or more eyes.

8. The composition of claim 1, wherein the composition is applied via at least one of an eye dropper and single use applicator.

* * * * *